United States Patent
Layser et al.

(10) Patent No.: US 9,931,447 B2
(45) Date of Patent: Apr. 3, 2018

(54) QUICK-OPENING VENT VALVE FOR PHACO FLUIDICS ASPIRATION SYSTEM

(71) Applicant: Novartis AG, Basel (CH)

(72) Inventors: Gregory S. Layser, Oceanside, CA (US); Daniel G. White, Irvine, CA (US); Satish Yalamanchili, Irvine, CA (US)

(73) Assignee: Novartis AG, Lichtstrasse, Basel (CH)

( * ) Notice: Subject to any disclaimer, the term of this patent is extended or adjusted under 35 U.S.C. 154(b) by 599 days.

(21) Appl. No.: 14/571,374

(22) Filed: Dec. 16, 2014

(65) Prior Publication Data

US 2016/0166742 A1  Jun. 16, 2016

(51) Int. Cl.
| | |
|---|---|
| *A61M 1/00* | (2006.01) |
| *A61M 3/02* | (2006.01) |
| *A61F 9/007* | (2006.01) |
| *F16K 5/04* | (2006.01) |
| *F16K 5/18* | (2006.01) |

(Continued)

(52) U.S. Cl.
CPC ....... *A61M 1/0058* (2013.01); *A61F 9/00745* (2013.01); *A61M 1/0033* (2014.02); *A61M 3/02* (2013.01); *F16K 5/0407* (2013.01); *F16K 5/18* (2013.01); *F16K 27/065* (2013.01); *A61M 2039/229* (2013.01); *A61M 2205/128* (2013.01); *A61M 2205/3334* (2013.01); *A61M 2210/0612* (2013.01)

(58) Field of Classification Search
CPC .............. A61M 1/0033; A61M 1/0058; A61M 2039/229; F16K 5/00
USPC .................................. 604/119; 251/207–209
See application file for complete search history.

(56) References Cited

U.S. PATENT DOCUMENTS

| | | | |
|---|---|---|---|
| 3,998,227 A | | 12/1976 | Holbrook et al. |
| 4,453,567 A | * | 6/1984 | MacDonald .............. F16K 3/08 |
| | | | 137/614.11 |

(Continued)

FOREIGN PATENT DOCUMENTS

| | | |
|---|---|---|
| DE | 19940471 A1 | 3/2001 |
| WO | 2010080894 A2 | 7/2010 |

(Continued)

OTHER PUBLICATIONS

Layser, Gregory S.; "Flow Control During Multi-Cavity Injection Molding Processes", Lehigh University Master Thesis, Apr./May 2004, Chapter 3, pp. 26-44.

*Primary Examiner* — Laura Bouchelle (57) ABSTRACT

Apparatuses, systems, and methods are provided for rapid venting of vacuum to mitigate occlusion break surge within a phaco fluidics aspiration system. The aspiration system may utilize a positive displacement pump to generate flow and a vent valve to vent or moderate the pressure or vacuum level based on pressure sensor feedback detected within the eye and at the pump. Embodiments described herein provide a quick-opening vent valve that produces a quick-opening flow response upon angular rotation of the quick-opening vent valve. The flow performance at the quick-opening vent valve is improved by increasing the effective cross-sectional area of the valve at near-closed valve positions. In particular, the increase in the cross-sectional area is achieved by forming a concaving edge portion to complement a circular edge of and opening of a flow channel formed through the vent valve.

13 Claims, 11 Drawing Sheets

(51) Int. Cl.
*F16K 27/06* (2006.01)
*A61M 39/22* (2006.01)

(56) References Cited

U.S. PATENT DOCUMENTS

| | | | |
|---|---|---|---|
| 5,009,393 | A | 4/1991 | Massey |
| 6,731,963 | B2 | 5/2004 | Finarov et al. |
| 6,808,162 | B2 | 10/2004 | Tranovich et al. |
| 7,565,918 | B2 | 7/2009 | Zamalis et al. |
| 9,549,850 | B2 | 1/2017 | Sorensen et al. |
| 9,561,321 | B2 | 2/2017 | Sorensen et al. |
| 2010/0152762 | A1 | 6/2010 | Mark |
| 2013/0150782 | A1* | 6/2013 | Sorensen ............ A61M 3/0283 604/30 |

FOREIGN PATENT DOCUMENTS

| | | |
|---|---|---|
| WO | 2013039742 A2 | 3/2013 |
| WO | 2013039742 A3 | 3/2013 |
| WO | 2016100083 A1 | 6/2016 |

* cited by examiner

QUICK-OPENING VENT VALVE FOR PHACO FLUIDICS ASPIRATION SYSTEM

BACKGROUND

The present disclosure relates generally to aspiration systems used in phacoemulsification procedures, and more particularly, to aspiration systems employing quick-opening vent valves to improve operation.

Typical surgical instruments suitable for phacoemulsification procedures on cataractous lenses include an ultrasonically driven phacoemulsification hand piece with a cutting needle and an irrigation sleeve, and a control console. The hand piece is attached to the control console by an electric cable and flexible tubing. The flexible tubing supplies irrigation fluid to the surgical site and carries aspiration fluid from the surgical site to a waste or discard reservoir.

During a phacoemulsification procedure, the tip of the cutting needle and the end of the irrigation sleeve are inserted into the anterior segment of the eye through a small incision in the eye's outer tissue. The surgeon brings the tip of the cutting needle into contact with the lens of the eye, so that the vibrating tip fragments the lens. The resulting fragments are aspirated out of the eye through the interior bore of the cutting needle, along with irrigation fluid provided to the eye during the procedure.

Throughout the procedure, irrigating fluid is infused into the eye, passing between the irrigation sleeve and the cutting needle and exiting into the eye at the tip of the irrigation sleeve and/or from one or more ports or openings formed into the irrigation sleeve near its end. This irrigating fluid is critical, as it prevents collapse of the eye during the removal of the emulsified lens, protects the eye tissue from the heat generated by the vibrating of the ultrasonic cutting needle, and suspends the fragments of the emulsified lens for aspiration from the eye.

During the surgical procedure, the console controls irrigation flow rates and aspiration flow rates to maintain a proper intra-ocular chamber pressure balance in an effort to maintain a relatively consistent fluid pressure at the surgical site in the eye.

Aspiration flow rates of fluid from the eye are typically regulated by an aspiration pump that creates a vacuum in the aspiration line. The aspiration flow and/or vacuum are set to achieve the desired working effect for the lens removal. While a consistent fluid pressure in the eye is desirable during the phacoemulsification procedure, common occurrences or complications create fluctuations or abrupt changes in fluid flow and pressure at the eye. Occlusion break surge is an undesirable shallowing of the anterior chamber of the eye that results when vacuum is generated within the aspiration pathway due to a flow obstruction and then that obstruction is suddenly removed. This results in a high demand for fluid from the eye to relieve the vacuum, causing a sudden shallowing of the anterior chamber.

The problem of occlusion surge has been addressed in the past in a number of ways including adding a reduced cross-section orifice in the aspiration line. While such a reduced area reduces the effects of occlusion surge, reduction of aspiration path cross-section can also increase the potential for clogging during the procedure. Other methods have been used or proposed that involve torturous paths, with corners, angles, and fluid restrictors that are also subject to clogging. Some prior solutions involve a resistive element at or near the pump. However, the effectiveness of these solutions is limited due to the relatively large tubing compliance between the resistive element and the eye.

Another attempted solution has been the use of increased lengths of flexible aspiration tubing in an attempt to increase overall tubing resistance. This solution of adding flexible tubing length has the undesirable effect of adding additional compliance to the aspiration path. The additional compliance increases the demand for fluid from the eye during occlusion break, sometimes entirely offsetting the benefits obtained by the longer tubing length.

Therefore, there remains a need for an improved system for reducing occlusion surge that that can occur during a medical procedure. The present disclosure is directed to addressing one or more of the deficiencies in the prior art.

SUMMARY

This disclosure relates generally to, and encompasses, apparatuses and methods for providing a vent valve for venting vacuum in an aspirating system to mitigate the amount of occlusion break surge. In particular, a vent valve with improved openings for the flow channel is provided to improve an initial flow rate when the vent valve is in a near closed position.

In an embodiment, a phacoemulsification surgical system may be provided with an improved vent valve that provides increased initial flow rate when the vent valve initially opens. The phacoemulsification surgical system may include an irrigation system configured to provide an irrigating fluid to a surgical site and an aspiration system arranged to aspirate an aspirating fluid from the surgical site. The aspiration system may include an aspiration path configured to direct the aspirating fluid away from the surgical site to the aspirating fluid drain and a cassette disposed in the aspiration path. The cassette may include a pump interface portion configured to pass the aspirating fluid along the aspiration path to the aspirating fluid drain. It may include a vent path connecting the aspiration path to a vent reservoir bypassing the pump interface portion, a valve chamber having a solid wall and a first opening in the solid wall, the first opening having a first edge portion between the solid wall and the first opening, and a vent valve disposed in the valve chamber configured to selectively rotate between an open position and a closed position, the valve chamber comprising a flow channel therethrough. The flow channel has a second opening selectively alignable with the solid wall in the closed position to prevent fluid flow therethrough and alignable with the first opening in the open position to permit fluid flow therethrough. The second opening of the vent valve has a second edge portion substantially complementary in shape to the first edge portion of the valve chamber. The first edge portion of the valve chamber and the second edge portion of the vent valve passes each other as the vent valve transitions from the closed position to the open position.

In an embodiment, the first opening of the valve chamber has a circular shape, and the second edge portion of the flow channel of the vent valve has a concave shape complementing the circular shape of the first opening of the valve chamber. In an embodiment, the concave shape of the second edge portion has a radius substantially the same as that of the circular shape of the first opening of the valve chamber. In some embodiments, the second opening of the flow channel has an hour-glass shape including the second edge portion as one of two concaving sides of the hour-glass shape. The complementing shapes of the first edge portion of the valve chamber and the second edge portion of the vent valve provide increased flow rate when the vent valve initially opens.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates to apparatuses, systems, and methods for rapid venting of vacuum to mitigate occlusion break surge within a phaco fluidics aspiration system. The aspiration system may utilize a positive displacement pump to generate flow and a vent valve to vent or moderate the pressure or vacuum level based on pressure sensor feedback detected within the eye and at the pump. Embodiments described herein provide a quick-opening vent valve that produces a quick-opening flow response upon angular rotation of the quick-opening vent valve. The flow performance at the quick-opening vent valve is improved by increasing the effective cross-sectional area of the valve at near-closed valve positions. In particular, the increase in area is achieved by incorporating two circular arcs with radii nearly equal to the barrel through hole. One of ordinary skill in the art, however, would understand that similar embodiments could be used to provide quick-opening flow response without departing from the general intent or teachings of the present disclosure.

Figure 1:
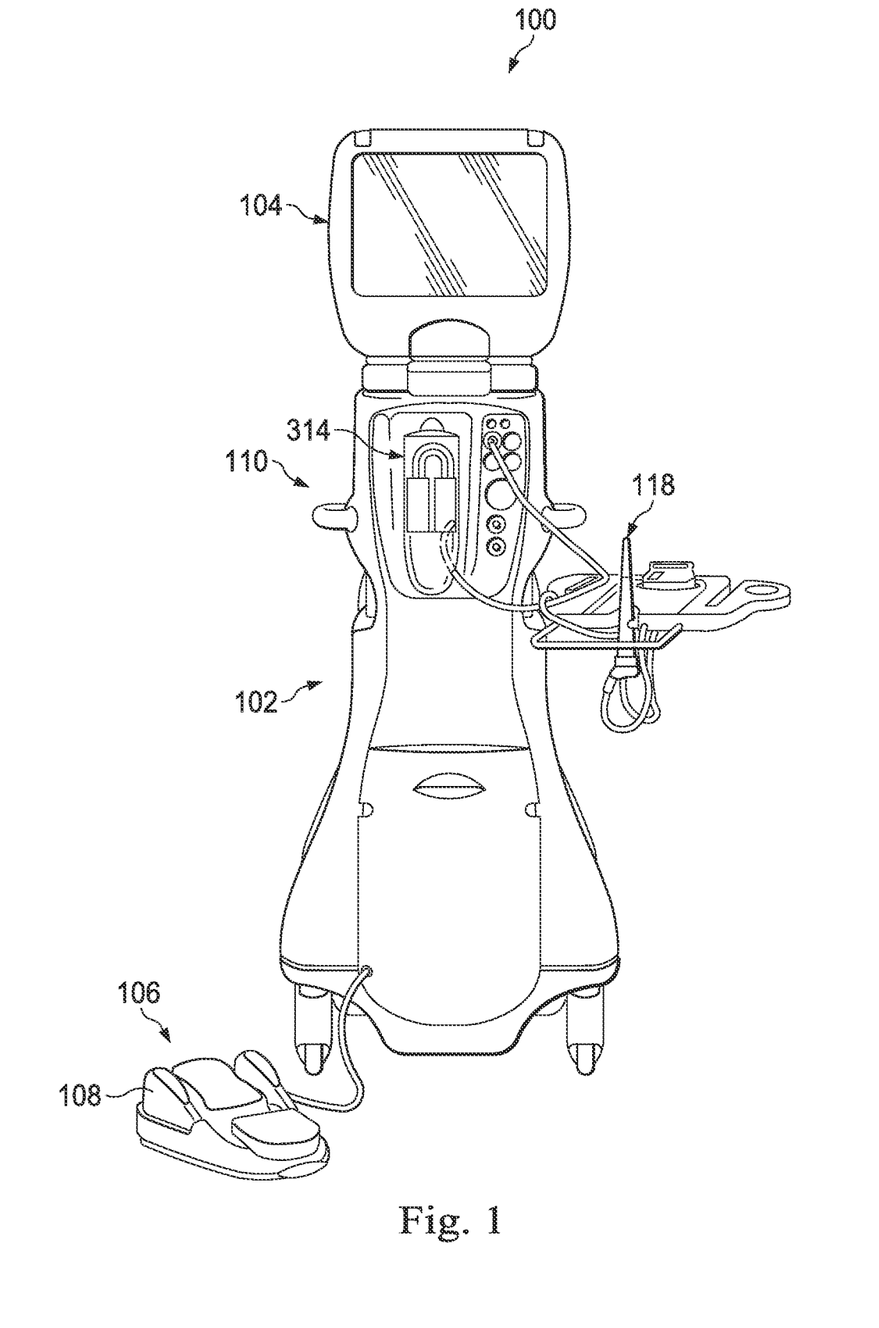
FIG. 1 is an illustration of an exemplary phacoemulsification surgical console according to one aspect of the present disclosure implementing the teachings and principles described herein.
Figure 2:
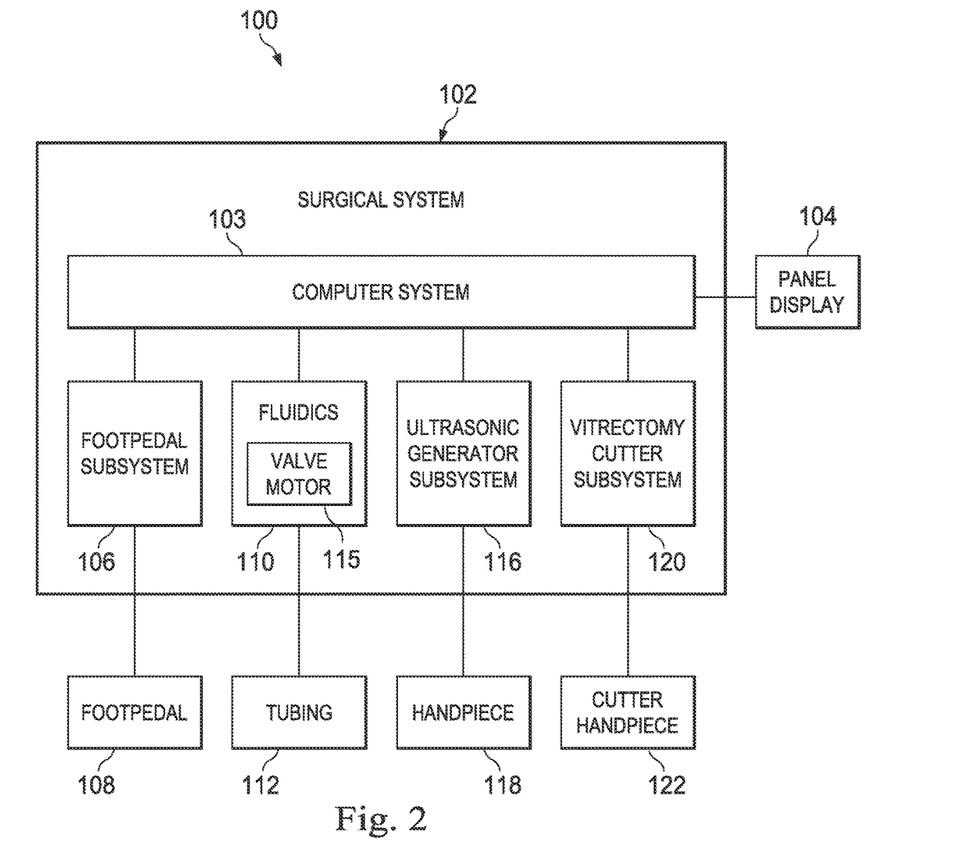
FIG. 2 is a block diagram of the phacoemulsification console of FIG. 1 showing various subsystems including a fluidics subsystem that drives aspiration according to the principles of the present disclosure.

FIG. 1 illustrates an exemplary emulsification surgical console, generally designated 100. FIG. 2 is a block diagram of the console 100 showing various subsystems that operate to perform a phacoemulsification procedure. The console 100 includes a base housing 102 with a computer system 103 disposed therein and an associated display screen 104 showing data relating to system operation and performance during an emulsification surgical procedure. The console 100 also includes a number of subsystems that are used together to perform an emulsification surgical procedure. For example, the subsystems include a foot pedal subsystem 106 including, for example, a foot pedal 108, a fluidics subsystem 110 including an irrigation system and an aspiration system that deliver fluid to and aspirate fluid from the eye through flexible tubing 112, an ultrasonic generator subsystem 116 including an ultrasonic oscillation hand piece 118 with a cutting needle, and a pneumatic vitrectomy cutter subsystem 120 including a vitrectomy hand piece 122. These subsystems overlap and cooperate to perform various aspects of the procedure.

Figure 3:
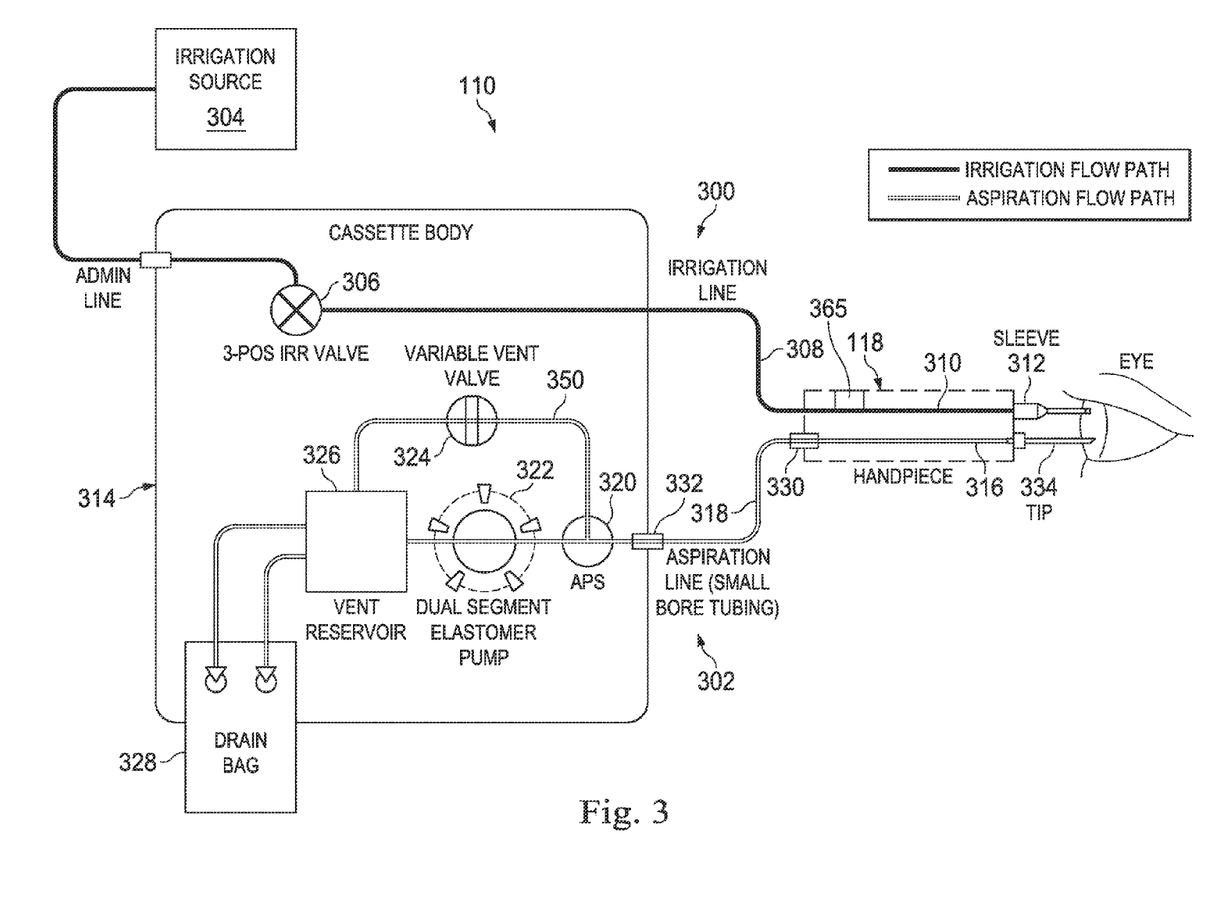
FIG. 3 is a schematic of an exemplary fluidics subsystem usable with the phacoemulsification surgical console of FIGS. 1 and 2 according to one aspect of the present disclosure.

FIG. 3 illustrates a schematic showing the fluidics subsystem 110 and the hand piece 118. The fluidics subsystem 110 includes an irrigation system 300 and an aspiration system 302, each in communication with the hand piece 118.

The irrigation system 300 includes an irrigation source 304 as a sterile solution reservoir, an irrigation valve 306 that regulates flow from the reservoir to the surgical site, a flexible irrigation tubing 308, an irrigation path 310 in the hand piece 118, and a sleeve 312 that may be considered a component of the hand piece 118. The irrigation source 304 may be a mechanically pressurized fluid source such as, for example, a clamping pressure system. In another embodiment, the irrigation source 304 may be a source suspended by a pole (e.g., an IV pole) which may or may not be adjustable. Other fluid sources also are contemplated.

The irrigation system 300 extends between the sterile solution reservoir 304 and the hand piece 118, and carries fluid to the surgical site (labeled in FIG. 3 as an eye). In one example, the sterile fluid is a saline fluid, however, other fluids may be used. The flexible irrigation tubing 308 may be formed in part of the flexible tubing 112 in FIG. 2. In some embodiments, the irrigation tubing 308 is formed of multiple segments, with some segments being rigid and others being flexible. Also, in some embodiments, at least a portion of the irrigation system 300 is formed in a cassette 314 that cooperates with the console 100 in FIG. 1 to provide fluid communication between the sterile solution reservoir 304 and the patient's eye. As indicated above, in some embodiments, the irrigation sleeve 312 is disposed about the cutting needle to provide irrigating fluid flow to the eye during the surgical procedure.

The aspiration system 302 includes an aspiration path 316 in the hand piece 118, a handpiece pressure sensor (HPS) 365 located within the hand piece 118, a small bore flexible aspiration tubing 318, an aspiration pressure sensor (APS) 320, a pump 322, a vent valve 324, a drain line reservoir 326, and a drain reservoir 328. In an embodiment, the HPS 365 may be disposed at the irrigation path of the hand piece 118. In another embodiment, the HPS 365 may be disposed at aspiration path of the hand piece 118. A hand piece connector 330 connects the aspiration path 316 in the hand piece 118 to the small bore flexible aspiration tubing 318. A cassette connector 332 connects the flexible aspiration tubing 318 to the cassette aspiration line in the cassette 314. As can be seen, the aspiration system 302 extends from the surgical site (eye) to the drain reservoir 328. It carries away fluid used to flush the eye as well as any emulsified particles. As described above with reference to the flexible irrigation tubing 308, at least a portion of the small bore flexible aspiration tubing 318 may be formed of the flexible tubing 112. In some embodiments, the aspiration system 302 is formed of multiple segments, with some segments being rigid and others being flexible. Also, in some embodiments, at least a portion of the aspiration system 302 is formed in the cassette 314 that cooperates with the console 100 in FIG. 1 to provide fluid communication between the hand piece 118 and the drain reservoir 328. It should be apparent that the drain reservoir 328 may in fact be a drain instead of a self-contained reservoir. As indicated above, in some embodiments, the aspiration system 302, including the aspiration fluid path 316, is in fluid communication with the bore of the cutting tip (labeled 334 in FIG. 3) of the hand piece 118 and is used to aspirate fluid and emulsified particles through the needle bore and into the aspiration system 302 during the surgical procedure.

When vacuum is generated within the aspiration pathway due to a flow obstruction, such as when lens fragments enter and clog portions of the aspiration pathway during a surgery, the surgical system 102 may detect the vacuum, or pressure difference, via pressure sensor 320 installed at the pump 322 and/or pressure sensor 365 installed in the hand piece 118.

The surgical system 102 may control the vent valve 324 to open to relieve the vacuum in the aspiration pathway and to reduce the effect of occlusion break. This would reduce the magnitude of resulting surge and maintain a predetermined level of vacuum so as not to lessen the efficiency of lens removal.

Figure 4:
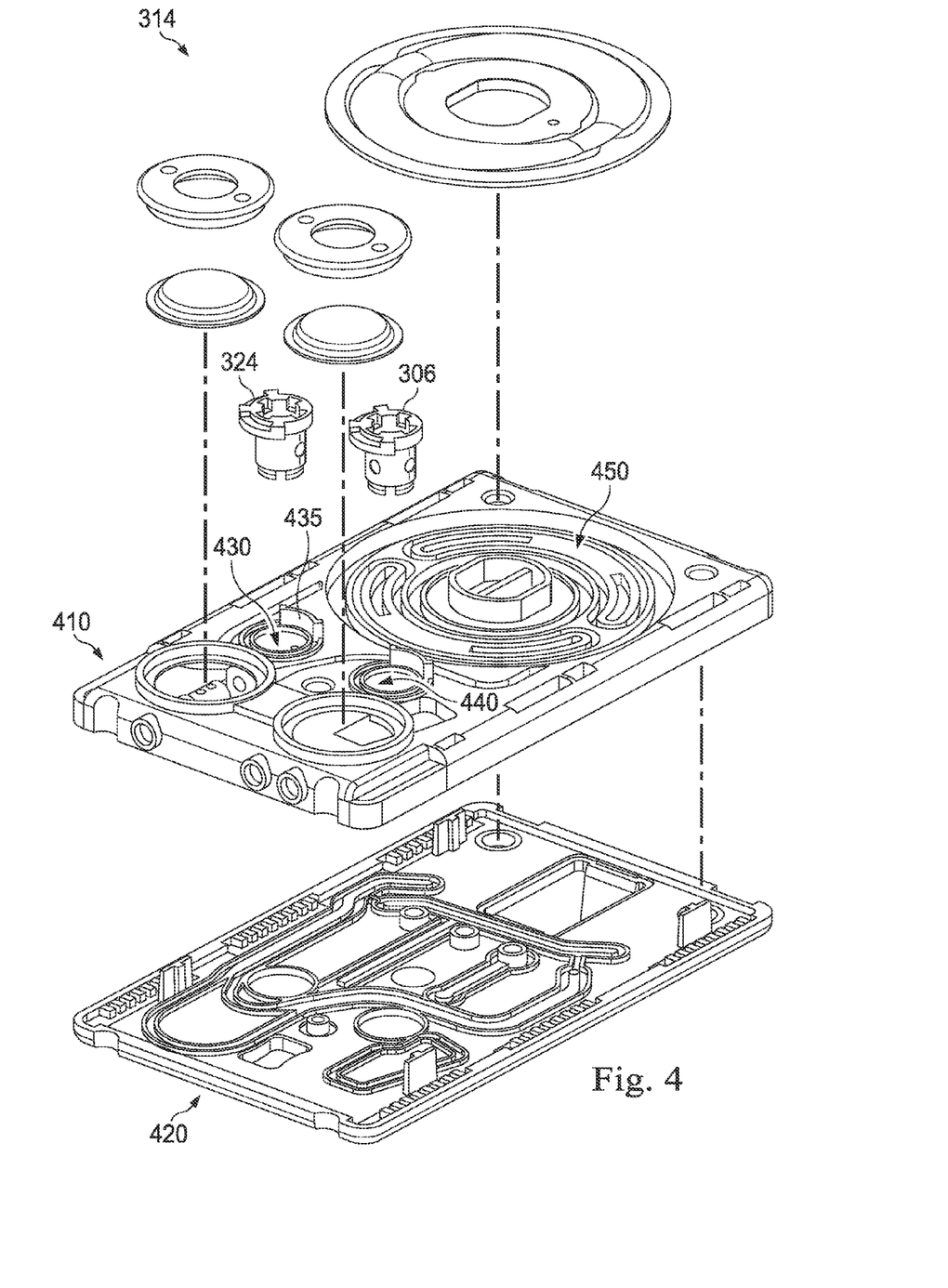
FIG. 4 is an exploded view of an exemplary cassette usable with the fluidics subsystem of FIG. 3 according to one aspect of the present disclosure.

FIG. 4 is an exploded view of an exemplary cassette 314 usable with the fluidics subsystem of FIG. 3 according to one aspect of the present disclosure. The body of cassette 314 may be formed by an upper housing 410 and a lower housing 420 coupled to each other. The housings 410 and 420 may be formed with rigid thermoplastic material, such as polycarbonate and/or polysulfone to provide rigidity and structure. A pump interface portion 450 may be disposed in cassette 314 to engage pump 322. Pump 322 may be an elastomer pump configured to drive fluid flow in the aspiration flow path. A vent valve chamber 430 and an aspiration valve chamber 440 also may be provided in the cassette. Vent valve chamber 430 may be configured to accommodate vent valve 324. Aspiration valve chamber 440 may be configured to accommodate irrigation valve 306.

Portions of irrigation flow path and aspiration flow path may extend as channels and/or tubes inside the body of cassette 314. Vent valve chamber 430 may be positioned in a vent path 350, such that vent valve 324 may selectively close and open to allow vacuum venting via the vent path 350. In some embodiments, the vent valve 324 is a rotary stopcock valve formed with high-density elastic polymer, such as polyethylene or acetal, such that vent valve 324 may be press-fit into vent valve chamber 430. Thus, vent valve 324 may rotate within the vent valve chamber 430 as driven by a valve motor 115 (e.g., a stepper motor or other motor type) with an angular position encoder to selectively open and close the vent path 350, as shown in FIG. 3.

Vent valve 324 typically may be in a closed position while performing a surgical procedure. When excessive vacuum is detected in the irrigation flow path, the valve motor 115 may be driven by a controller or computer system 103 to rotate vent valve 324 from the closed position to an open position to open the vent path 350 for vacuum venting. The response speed of vacuum venting is important for minimizing the onset of occlusion surge. Although rotating the valve motor 115 faster could potentially achieve faster venting, this approach is limited by the motor speed and controller response time. The embodiments of the disclosure provide improved vent valve structures for quick-opening and quick-closing flow characteristics at near-closed valve positions.

Figure 5A:
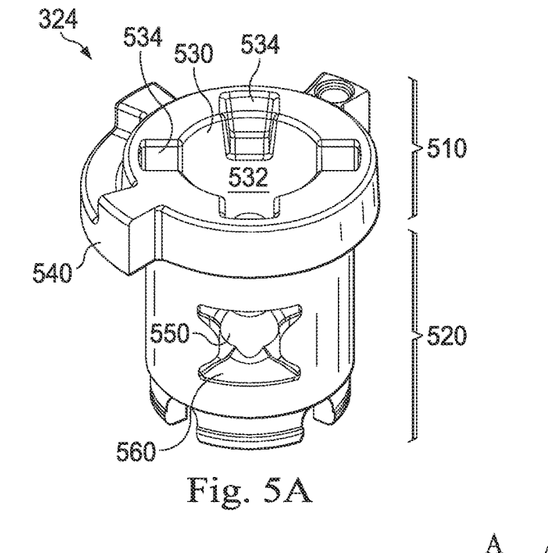
FIG. 5A is a diagram showing an illustrative perspective view of a quick-opening vent valve according to one aspect of the present disclosure.
Figure 5B:
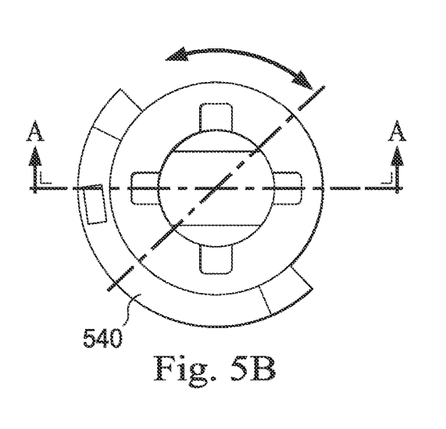
FIG. 5B is a diagram showing a top view of the quick-opening vent valve of FIG. 5A according to one aspect of the present disclosure.

FIG. 5A is a diagram showing an illustrative perspective view of a quick-opening vent valve 324 according to one aspect of the present disclosure. Vent valve 324 may include a motor engagement portion 510 and a body portion 520. Motor engagement portion 510 may include an axle interface 530 configured to engage a driving axle of a valve motor 115. As shown in FIGS. 5A and 5B, the axle interface 530 may include a substantially cylindrical chamber 532 for receiving the driving axle of the valve motor 115. Cross shape cutouts 534 also may be provided at a top perimeter portion of the cylindrical chamber 532 to provide better torque engagement with the driving axle of the valve motor 115 during rotation. When the cassette 314 is installed onto the surgical system 102, the valve motor for driving the vent valve may engage the motor engagement portion 510 of the vent valve 324 installed in the cassette 314. In particular, a driving axle of the valve motor 115 may be inserted into the axle interface 530 of the vent valve 324. As such, the valve motor 115 may rotate the vent valve 324 via the driving axle.

Motor engagement portion 510 may also include a rotation restriction portion 540 provided at certain perimeter portion of the motor engagement portion 510. The rotation restriction portion 540 may define a rotation range of the vent valve 324 in coordination with a rotation stopper 435 provided on a top portion of vent valve chamber 430, as shown in FIG. 4. In particular, when vent valve 324 is installed in the vent valve chamber 430, the body portion 520 of the vent valve 324 may be accommodated inside the vent valve chamber 430 while the motor engagement portion 510 of the vent valve 324 may protrude from the vent valve chamber 430. As the vent valve 324 is rotated, the rotation restriction portion 540 may rotatably slide along an outer perimeter surface of the vent valve chamber 430. The rotation may be stopped when the sliding of the rotation restriction portion 540 bumps into the rotation stopper 435. As such, the rotation restriction portion 540 and the rotation stopper 435 together may define the rotation range of the vent valve 324. In some embodiments, the rotation range of the vent valve 324 may be defined based on an open position and a closed position of the vent valve 324.

Figure 5C:
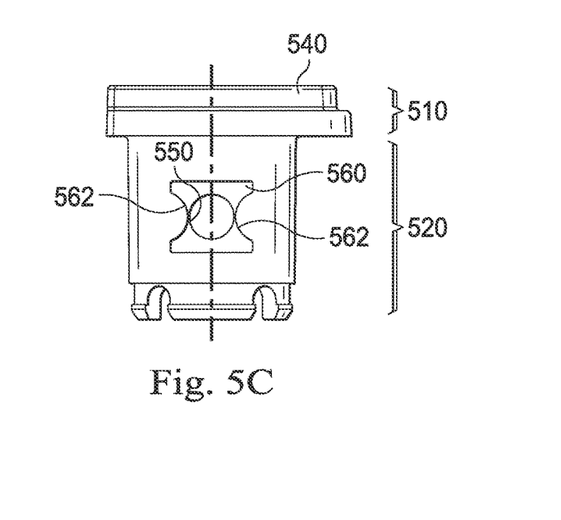
FIG. 5C is a diagram showing a side view of the quick-opening vent valve of FIG. 5A according to one aspect of the present disclosure.

The body portion 520 of the vent valve 324 may have a cylindrical shape solid surface 570 including a flow channel 550 formed there through. The flow channel 550 may have channel openings 560. The flow channel 550 may be configured to allow flow of aspiration fluid when the vent valve 324 is open. As shown in FIG. 5C, a side view of the quick-opening vent valve of FIG. 5A according to one aspect of the present disclosure, the flow channel 550 may have a substantially circular cross sectional shape. In another embodiment, the flow channel 550 may have a substantially square or rectangular shape. In this embodiment, opening portions 560 of the flow channel 550 have an hour-glass shape formed in the solid surface 570. As shown in FIG. 5C, the hour-glass shape is formed by a flat top side and a flat bottom side connected by two curved sides 562. The curved sides 562 may have a shape complementary or have an inverse shape to the shape of openings formed in the inner side walls of the vent valve chamber 430. In particular the radius of curvature of curved sides 562 may substantially be the same as that of the radius of the circular opening formed in the inner side walls of the vent valve chamber 430.

Figure 5D:
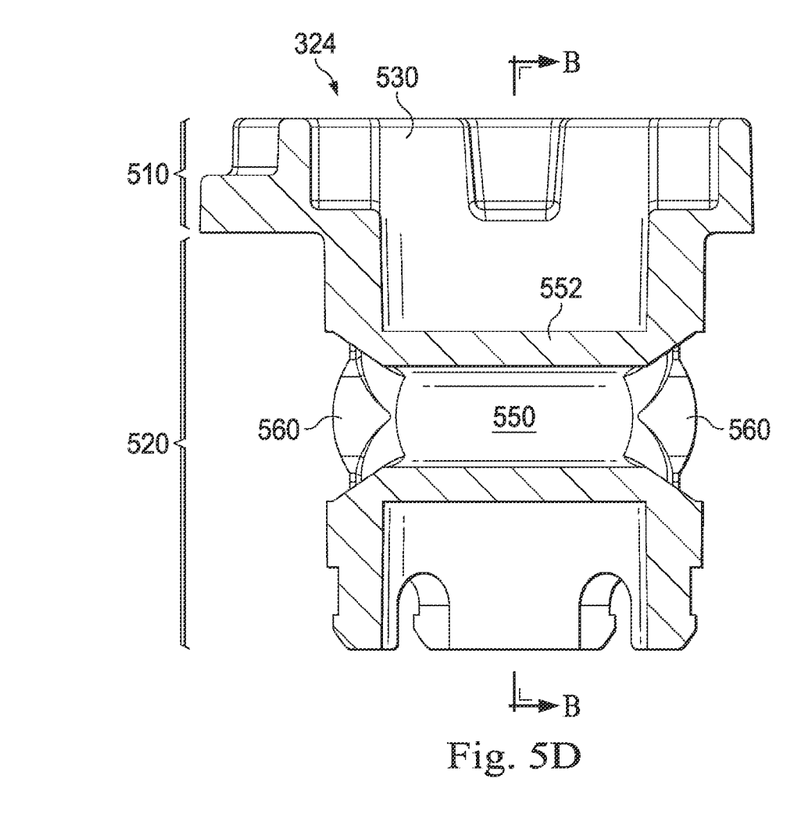
FIG. 5D is a diagram showing a cross-sectional view of the quick-opening vent valve of FIG. 5B taken along line A-A according to one aspect of the present disclosure.
Figure 5E:
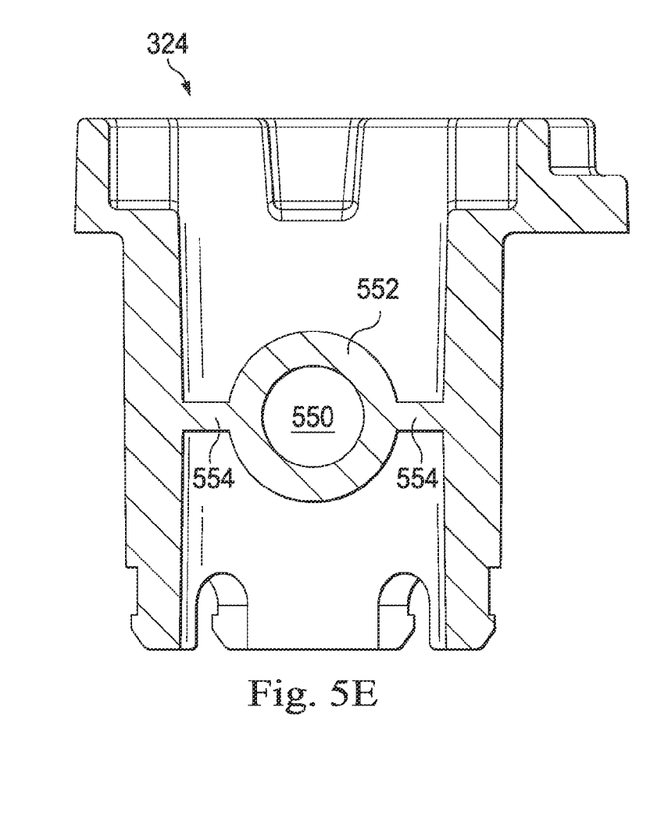
FIG. 5E is a diagram showing a cross-sectional view of the quick-opening vent valve of FIG. 5D taken along line B-B according to one aspect of the present disclosure.

FIG. 5D is a diagram showing a cross-sectional view of the quick-opening vent valve 324 taken along line A-A in FIG. 5B according to one aspect of the present disclosure. The opening portions 560 may have a larger cross-sectional area than that of the flow channel 550. The hour-glass shape opening portions 560 may gradually transition in a sloping manner to the circular shape flow channel 550. The larger hour-glass shape openings 560 may provide additional space that may serve as a dam to hold additional fluid within the vent valve 324 when the vent valve 324 is in the closed position. The additional fluid held in the dam may provide additional fluid volume when the vent valve 324 initially opens to provide quick flow response for vacuum venting. FIG. 5E is a diagram showing a cross-sectional view of the quick-opening vent valve 324 taken along line B-B in FIG. 5D according to one aspect of the present disclosure. The flow channel 550 may have a substantially circular cross sectional shape and may be formed in an inner circular pipe portion 552. Inner circular pipe portion 552 may be supported by bridge extensions 554 extending from the inner side walls of vent valve 324. In another embodiment, the flow channel 550 may have a substantially rectangular or square cross sectional shape. Other cross sectional shapes are also contemplated for the flow channel 550.

Figure 6A:
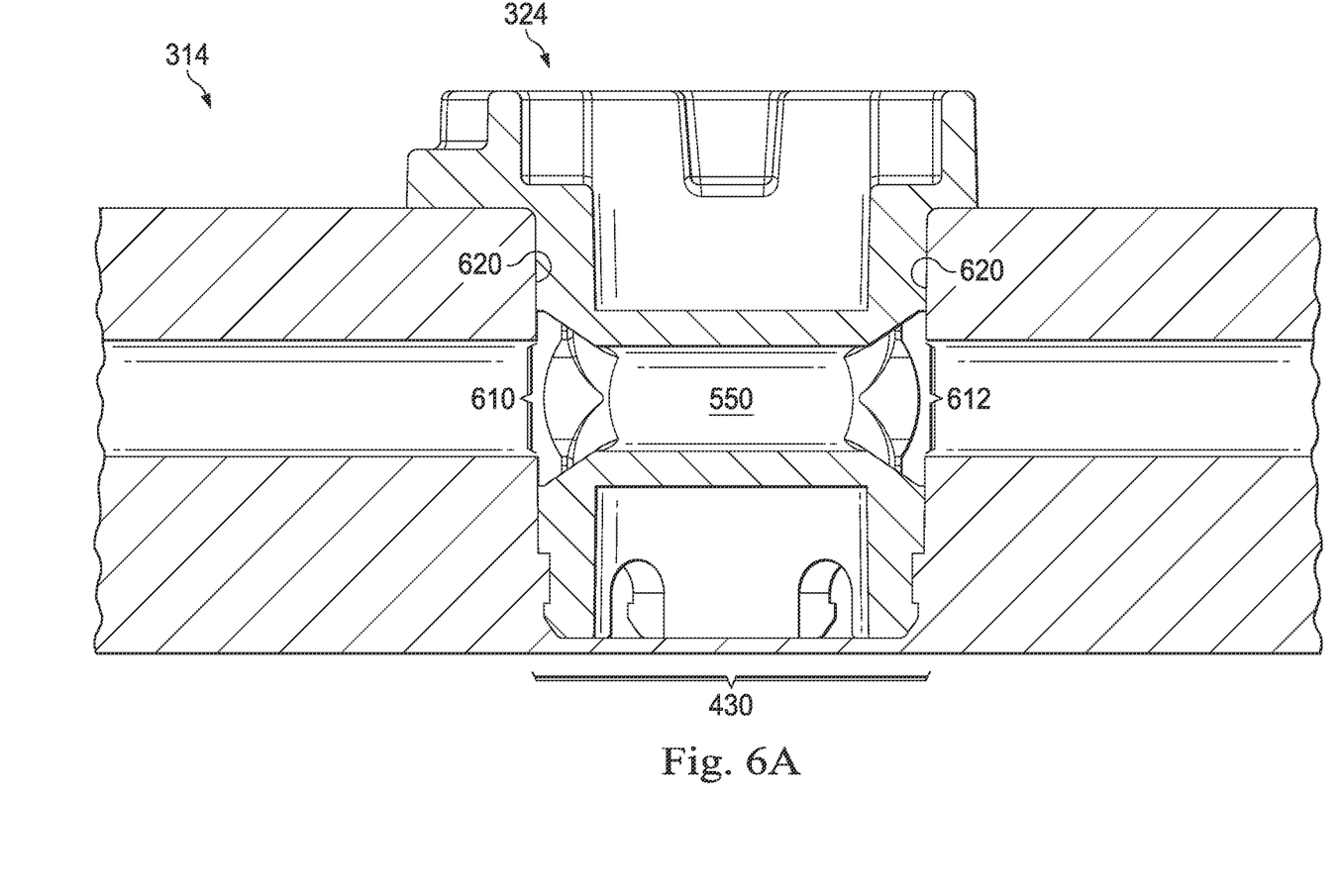
FIG. 6A is a diagram showing a cross-sectional view of the quick-opening vent valve of FIG. 5A installed in a valve chamber in an open position according to one aspect of the present disclosure.
Figure 6B:
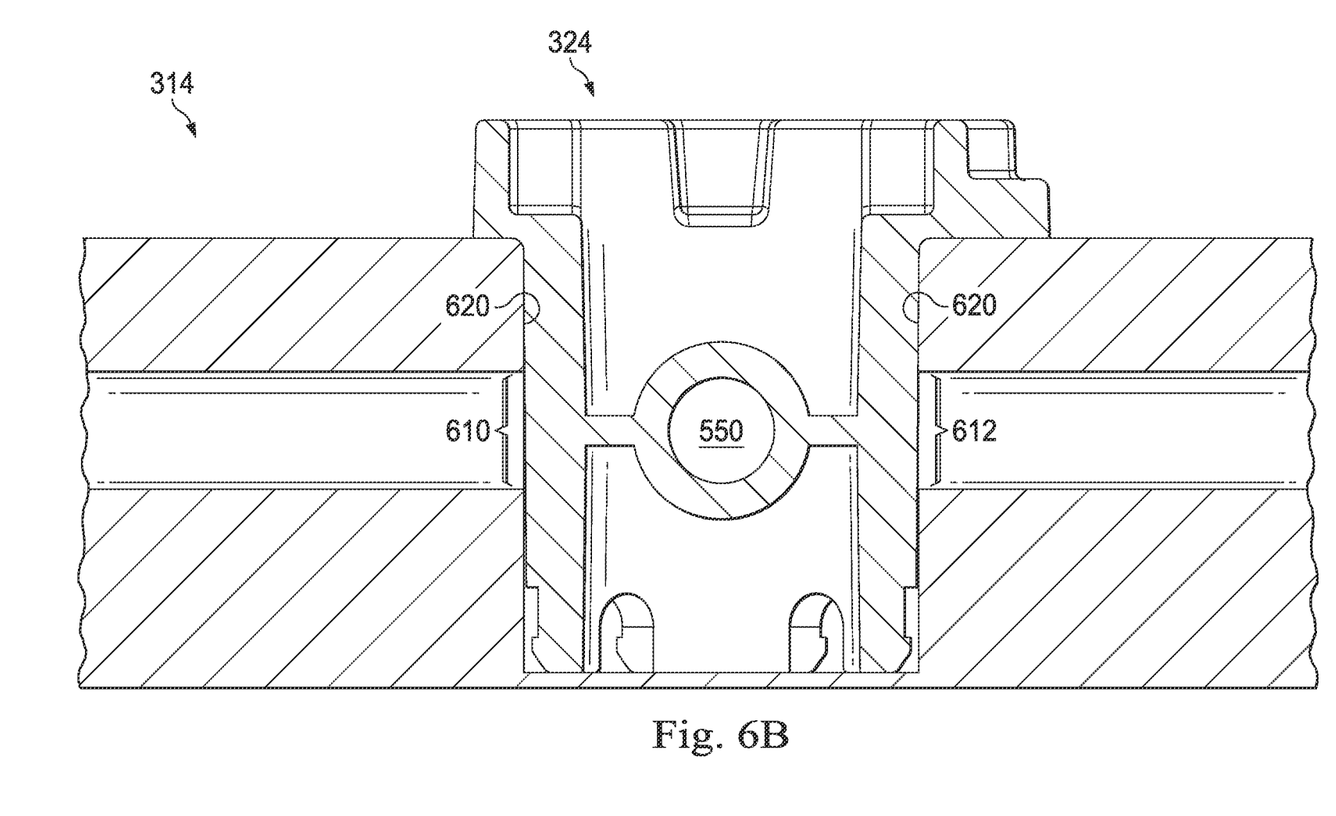
FIG. 6B is a diagram showing a cross-sectional view of the quick-opening vent valve of FIG. 5A rotated 90 degrees which is installed in the valve chamber of FIG. 6A in a closed position according to one aspect of the present disclosure.
Figure 6C:
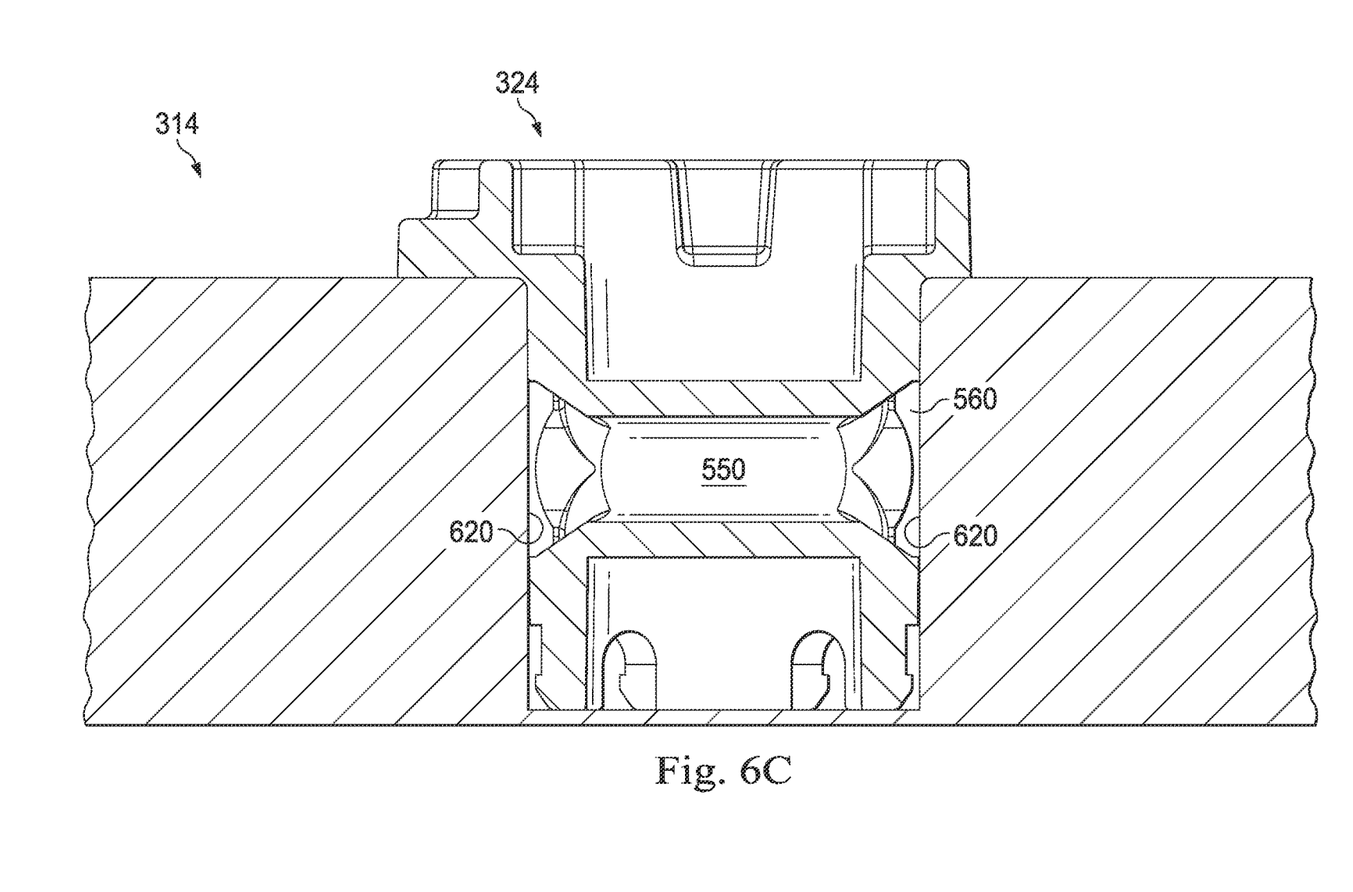
FIG. 6C is a diagram showing a cross-sectional view of the quick-opening vent valve of FIG. 5A which is installed in a valve chamber in a closed position and taken at a 90 degree section relative to FIG. 6B according to one aspect of the present disclosure.

FIG. 6A is a diagram showing a cross-sectional view of the quick-opening vent valve taken along line A-A of FIG. 5A which is installed in a vent valve chamber 430 of a cassette in an open position according to one aspect of the present disclosure. Vent valve chamber 430 may include openings 610 and 612 formed in the inner side of solid walls 620 across from each other to face each other. In the open position, one of openings 610 and 612 may lead to the vent reservoir side of the vent path 350 and the other may lead to the aspiration flow path. Based on the position of the vent valve 324, the openings 610 and 612 may be selectively connected to each other via flow channel 550 of vent valve 324. For example, as shown in FIG. 6A, when vent valve 324 is rotated such that the openings 560 of vent valve 324's flow channel 550 correspond to or is aligned with the openings 610 and 612 of the valve chamber 430, the vent valve 324 is in an open position and the vent path 350 is open to allow fluid flow or vacuum venting. On the other hand, as shown in FIG. 6B, when vent valve 324 is rotated such that the openings 560 of vent valves 324's flow channel 550 is rotated away or offset from the openings 610 and 612 of the valve chamber 430, the vent valve 324 is in a closed position and the vent path 350 is closed to stop vacuum venting. The openings 610 and 612 may align with solid surface 570 of the vent valve 324 in the closed position to prevent fluid flow at the openings 610 and 612. As shown in FIG. 6C, the openings 560 of vent valves 324's flow channel 550 are aligned with the inner surfaces of the solid walls 620 in the closed position to prevent fluid flow through the openings 560 and to stop vacuum venting.

When vacuum is building up in the aspiration flow path due to obstructions, such as lens fragments, the pressure sensors 320 and 365 may detect the vacuum buildup and the system may control the vent valve 324 to open to relieve the vacuum through the vent path 350, as shown in FIG. 3. A quick response time may allow quick venting of vacuum to minimize occlusion break surge. The openings 560 of the flow channel 550 of the vent valve 324 are improved to have shapes that are complementary to the openings 610 and 612 of the valve chamber 430. In particular, the hour-glass shape of the openings 560 of flow channel 550 have a concave edge portion to complement the circular shape of the openings 610 and 612 of the valve chamber 430.

Figure 7A:
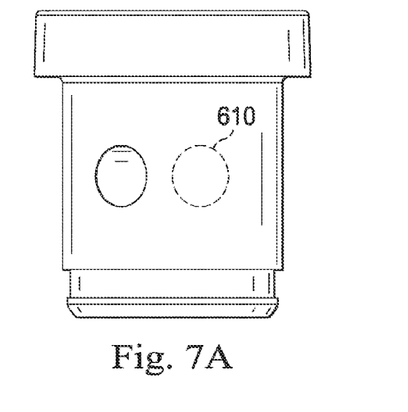
FIGS. 7A and 7B are diagrams showing a conventional vent valve transitioning from a closed position to a near-closed position according to one aspect of the present disclosure.
Figure 7B:
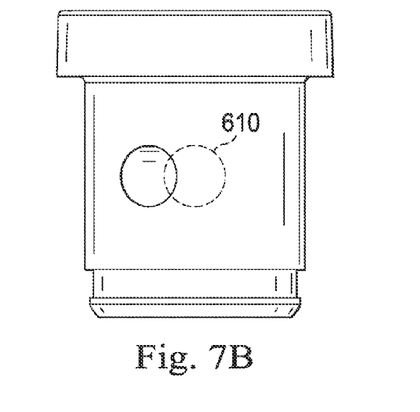

As shown in FIGS. 7A and 7B, the flow channel of a conventional vent valve has circular shape openings. The openings formed in the inner side walls of the valve chamber 430 also have circular shapes. As shown in FIG. 7A, when the conventional vent valve is closed, the vent valve's circular opening is offset from the opening of the valve chamber 430 (shown in dashed line). As the conventional vent valve rotates to open, the circular opening of the conventional vent valve begins to move and overlap with the circular opening of the valve chamber 430. The overlapping area is the cross sectional area through which the fluid may begin to flow to vent the vacuum. As shown in FIG. 7B, the overlapping area between the circular openings is relatively small for the conventional vent valve at the initial opening position or at the near closed position.

Figure 7C:
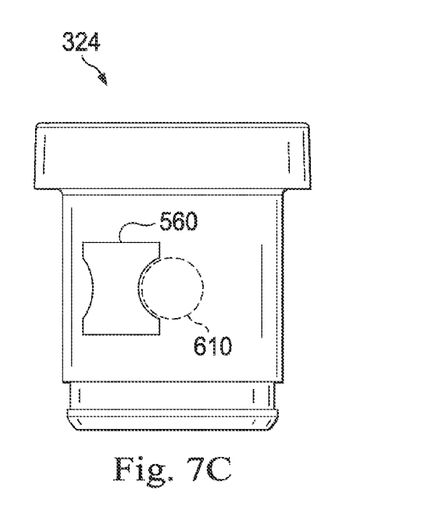
FIGS. 7C and 7D are diagrams showing a quick-open vent valve transitioning from a closed position to a near-closed position according to one aspect of the present disclosure.
Figure 7D:
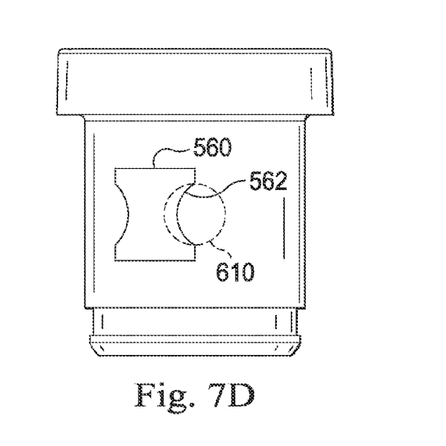

Referring now to FIGS. 7C and 7D, the improved vent valve 324 is a quick-opening valve that allows for increased flow at the initial opening position or at the near closed position. As shown in FIG. 7C, the opening 560 of vent valve 324's flow channel 550 has an hour-glass shape. In particular, the side edge portion 562 of the opening 560 has a concave shape with a radius substantially the same as that of the circular shape of valve chamber 430's opening 610. As such, in the closed position, the side edge 562 of vent valve 324's opening 560 closely tracks or complements the circular edge portion of valve chamber 430's opening 610. When the vent valve 324 begins to rotate from the closed position to the open position, the side edge portion 562 of vent valve 342's opening 560 begins to move pass a side edge portion of the opening 610 of valve chamber 430. Because of the longer complementary edge portions between vent valve 324's opening 560 and valve chamber 430's opening 610, the overlapping area is larger to provide greater flow at the initial opening position.

Figure 8A:
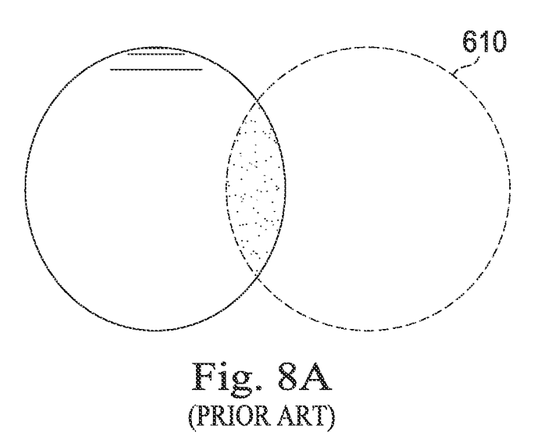
FIGS. 8A and 8B are diagrams of overlapping areas of openings comparing initial flow areas of the conventional vent valve and the improved quick-open vent valve according to one aspect of the present disclosure.
Figure 8B:
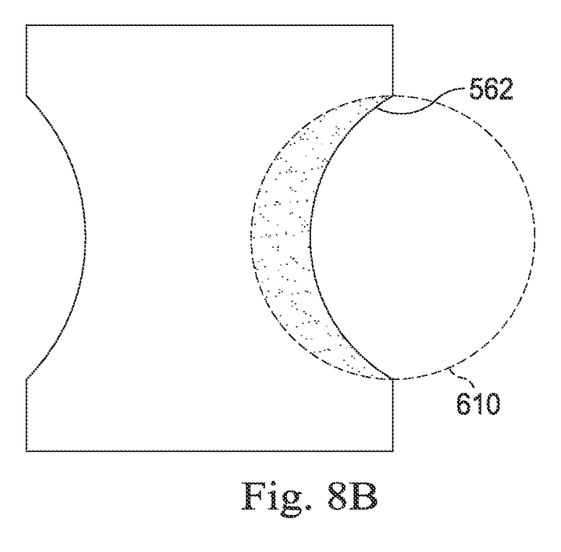

As shown in FIGS. 8A and 8B, for the same degree of rotation, the quick-opening vent valve 342 with the hour-glass shape openings 562 may allow for up to five times more initial flow than the conventional vent valve with the circular openings. The greater initial flow allows faster vacuum venting response to the aspiration flow path. Similarly, the improved opening shape at the vent valve 324 also may allow faster response when closing the valve. Similar features also may be applied to the interface between opening 560 of vent valve 324 and opening 612 of valve chamber 430.

While the above embodiments are described in view of the vent valve 324, similar features may be adapted for the irrigation valve 306. The above embodiments may provide an hour-glass shape opening at the vent valve 324 to complement the circular shape opening at the valve chamber 430. In some embodiments, the openings at the vent valve 324 may have circular shape while the openings at the valve chamber 430 have the complementary hour-glass shape.

While the above embodiments utilize an hour-glass shape opening at the vent valve 324 to improve initial flow, other opening shapes also may be utilized. The opening shapes at the vent valve 324 may be modified based on the opening shape at the valve chamber 430 such that they complement each other, e.g., inverse shape. For example, the valve chamber 430 may have an oval opening shape. As such, the vent valve 324 may be modified to have concave side edges of different radius accordingly.

The embodiments disclosed herein provide improved opening shapes for the vent valve to improve the initial flow rate. The increased initial flow rate may improve the response time for venting the excessive vacuum in the aspiration flow path to minimize occlusion break surge. This may lead to better patient outcome and surgical results.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A phacoemulsification surgical system, comprising:
   an irrigation system configured to provide an irrigating fluid to a surgical site; and
   an aspiration system arranged to aspirate an aspirating fluid from the surgical site, the aspiration system comprising:
      an aspiration path configured to direct the aspirating fluid away from the surgical site to an aspirating fluid drain; and
      a cassette disposed in the aspiration path, the cassette comprising:
         a pump interface portion configured to pass the aspirating fluid along the aspiration path to the aspirating fluid drain;
         a vent path connecting the aspiration path to a vent reservoir bypassing the pump interface portion;
         a valve chamber having a solid wall and a first opening in the solid wall, the first opening having a first edge portion between the solid wall and the first opening;
         a vent valve disposed in the valve chamber and configured to selectively rotate between an open position and a closed position, the vent valve comprising a flow channel therethrough, the flow channel having a second opening selectively alignable with the solid wall in the closed position to prevent fluid flow therethrough and alignable with the first opening in the open position to permit fluid flow therethrough, the second opening of the vent valve having a second edge portion substantially complementary in shape to the first edge portion of the valve chamber, wherein the first edge portion of the valve chamber and the second edge portion of the vent valve pass each other as the vent valve transitions from the closed position to the open position;
      wherein one of the first edge portions and the second edge portions has a convex shape;
      wherein the other of the first edge portion and the second edge portion has a concave shape complementing the convex shape;
      wherein the concave shape has a radius substantially the same as that of a circular shape; and
      wherein the second opening of the flow channel comprises the concave shape and has an hour-glass shape including two concaving sides of the hour-glass shape.

2. The phacoemulsification surgical system of claim 1, wherein the flow channel has a circular cross sectional shape; and
   wherein the second opening of the flow channel transitions gradually from the hour-glass shape to the circular cross sectional shape of the flow channel.

3. The phacoemulsification surgical system of claim 1, wherein the vent valve is a rotary cock stop valve.

4. The phacoemulsification surgical system of claim 1, further comprising:
   a motor configured to rotate the vent valve between the open position and the closed position to selectively open and close the vent path;
   a pressure sensor disposed in the hand piece and configured to detect a fluid pressure; and
   a controller configured to detect a vacuum in the aspirating fluid via the pressure sensor and control the motor to rotate the vent valve from the closed position to the open position when the vacuum is detected.

5. The phacoemulsification surgical system of claim 4, wherein the vent valve further comprises:
   a motor engagement portion configured to engage the motor when the cassette is installed onto the phacoemulsification surgical system; and
   a body portion through which the flow channel is formed, wherein, when the vent valve is installed in the valve chamber, the body portion of the vent valve is disposed within the valve chamber and the motor engagement portion protrudes from the valve chamber.

6. The phacoemulsification surgical system of claim 5,
wherein the motor engagement portion of the vent valve comprises a rotation restriction portion configured to slide on a top surface of the valve chamber when the vent valve rotates,
wherein the valve chamber further comprises a rotation stopper disposed on the top surface of the valve chamber, and
wherein the rotation stopper is configured to stop a rotation of the vent valve by stopping when the rotation restriction portion of the vent valve slides up against the rotation stopper.

7. The phacoemulsification surgical system of claim 6, where a rotation range of the vent valve is defined by positions and sizes of the rotation stopper of the valve chamber and the rotation restriction portion of the vent valve.

8. A cassette for use in an aspiration system of a phacoemulsification surgical system, comprising:
a pump interface portion configured to pass an aspirating fluid along an aspiration path;
a vent path connecting the aspiration path to a vent reservoir bypassing the pump interface portion;
a valve chamber having a solid wall and a first opening formed in the solid wall, the first opening having a first edge portion between the solid wall and the first opening; and
a vent valve disposed in the valve chamber and configured to selectively rotate between an open position and a closed position, the valve chamber comprising a flow channel therethrough, the flow channel having a second opening selectively alignable with the solid wall in the closed position to prevent fluid flow therethrough and alignable with the first opening in the open position to permit fluid flow therethrough, the second opening of the vent valve having a second edge portion substantially complementary in shape to the first edge portion of the valve chamber, wherein the first edge portion of the valve chamber and the second edge portion of the vent valve passes each other as the vent valve transitions from the closed position to the open position;
wherein one of the first edge portion and the second edge portion has a convex shape, and
wherein the other of the first edge portion and the second edge portion has a concave shape complementing the convex shape;
wherein the concave shape has a radius substantially the same as that of the convex shape;
wherein the concave shape comprises an hour-glass shape including two concaving sides of the hour-glass shape.

9. The cassette of claim 8,
wherein the flow channel has a circular cross sectional shape; and
wherein the second opening of the flow channel transitions gradually from the hour-glass shape to the circular cross sectional shape of the flow channel.

10. The cassette of claim 8, wherein the vent valve is a rotary cock stop valve.

11. The cassette of claim 8, wherein the valve chamber is formed with a first thermoplastic material and the vent valve is formed with a second thermoplastic material less rigid than the first thermoplastic material, such that the vent valve is press fit into the valve chamber.

12. A rotary vent valve for use in a cassette installed in an aspiration system of a phacoemulsification surgical system, the rotary vent valve comprising:
a motor engagement portion configured to engage a motor by which the rotary vent valve is rotated; and
a body portion through which a flow channel and two openings of the flow channel are formed, wherein an edge portion of at least one of the two openings of the flow channel has a concave shape;
wherein the at least one of the two openings of the flow channel has an hour-glass shape including the edge portion as one of two concave sides of the hour-glass shape.

13. The rotary vent valve of claim 12, wherein the flow channel has a circular cross sectional shape and the at least one of the two openings of the flow channel transitions gradually from the hour-glass shape to the circular shape of the flow channel.

* * * * *